United States Patent [19]

Kyriacou et al.

[11] 4,217,185

[45] Aug. 12, 1980

[54] ELECTROLYTIC PRODUCTION OF CERTAIN TRICHLOROPICOLINIC ACIDS AND/OR 3,6-DICHLOROPICOLINIC ACID

[75] Inventors: Demetrios Kyriacou, Clayton; Fred Y. Edamura, Concord; Jim Love, Walnut Creek, all of Calif.

[73] Assignee: The Dow Chemical Company, Midland, Mich.

[21] Appl. No.: 54,130

[22] Filed: Jul. 2, 1979

[51] Int. Cl.² .......................... C25B 3/04; C25B 11/04
[52] U.S. Cl. .................................. 204/73 R; 204/292
[58] Field of Search ........................... 204/73 R, 59 R

[56] References Cited

U.S. PATENT DOCUMENTS

| 3,677,916 | 7/1972 | Seiber | 204/59 R |
| 3,687,826 | 8/1972 | Seiber | 204/73 R |
| 3,694,332 | 9/1972 | Parker | 204/73 R |

*Primary Examiner*—F. C. Edmundson
*Attorney, Agent, or Firm*—R. R. Stringham

[57] ABSTRACT

Electrolytic reduction of tetrachloro-2-picolinic acid in basic aqueous solution, at an activated silver cathode, yields the 3,4,6- and 3,5,6-trichloro-2-picolinic acids, which in turn may be further reduced to 3,6-dichloropicolinic acid, a highly active herbicide.

15 Claims, No Drawings

ELECTROLYTIC PRODUCTION OF CERTAIN TRICHLOROPICOLINIC ACIDS AND/OR 3,6-DICHLOROPICOLINIC ACID

BACKGROUND OF THE INVENTION 3,6-Dichloropicolinic acid is disclosed in U.S. Pat. No. 3,317,549, as a highly active plant growth regulator which can be made by acid hydrolysis of 3,6-dichloro-2-(trichloromethyl)-pyridine.

In the approximately twelve years since the U.S. Pat. No. 3,317,549 patent issued, 3,6-dichloropicolinic acid (3,6-D, henceforth) has become increasingly of interest, particularly for control of weeds which can tolerate phenoxy-type herbicides—such as 2,4-D and MCPA. Thus, Canada thistle, Russian smartweed and wild buckwheat—for example—are susceptible to 3,6-D. The latter compound also has shown good activity on rangeland brush species, such as velvet mesquite, catclaw acacia and whitehorn. 3,6-D not only has a low toxicity to mammals, fish and birds, but is also relatively short lived in soil.

However, realization of the full potential of 3,6-D requires the development of a more efficient and economic method of synthesis than the preparation and hydrolysis of the corresponding trichloromethyl compound.

A substantially better method of preparing 3,6-D involves the reduction of 3,4,5,6-tetrachloropicolinic acid by successive reactions with hydrazine and an aqueous base, as described in U.S. Pat. No. 4,087,431. However, the efficiency of materials utilization in this process leaves something to be desired and the process cost is relatively high to be borne by an economic herbicide.

Another method which could be considered is electrolytic reduction of 3,4,5,6-tetrachloropicolinic acid. This of course would require replacement of both the 4 and 5 chlorines with hydrogen, under conditions such that hydrolysis (which is facile) and/or decarboxylation would not occur to any substantial extent. It would also require that over reduction, i.e., reduction of the 3,6-dichloropicolinic acid end-product—would not occur to a significant extend under the conditions required to effect the desired reduction.

U.S. Pat. No. 3,694,332 teaches that the 4-chlorine in tetrachloro-2-cyanopyridine can be replaced by hydrogen if the latter compound is co-dissolved with a neutral or acidic electrolyte (and water, as necessary) in an organic solvent and subjected to electrolytic reduction at a mercury (or lead) cathode. The patent also teaches that the same method may be used to reduce pentachloropyridine to 2,3,5,6-tetrachloropyridine (with coproduction of a small proportion of an unidentified trichloropyridine). The use of strong bases as electrolytes in the patented process is indicated as likely to result in hydrolysis reactions.

A co-pending application, Ser. No. 029,600, filed Apr. 13, 1979, in the name of D. Kyriacou as inventor, discloses that the electrolytic reduction of pentachloropyridine, co-dissolved with an aqueous base in an organic solvent and at a highly specific silver cathode, results in the replacement of the 4-chlorine, and then the 6- (or 2-) chlorine, with hydrogen.

No more pertinent prior art then the foregoing U.S. Pat. No. 3,694,332 patent is known of and the teachings of the patent and the aforesaid application fail to suggest to those knowledgeable in the prior art that tetrachloro-2-picolinic acid ("tet-acid") can be electrolytically reduced to the 3,6-dichloro acid (3,6-D) or to a trichloro-acid which will yield 3,6-D upon reduction. It may also be noted that attempts to electrolytically reduce several other polychloro-pyridine carboxylic acids in aqueous base solutions have failed, even when a siver cathode of the above mentioned type was employed. Similarly, attempts to so reduce a variety of chlorinated benzoic acids and phenols also were unsuccessful.

3,5,6-Trichloropicolinic acid ("3,5,6-T") is also a known compound which has herbicidal activity but for which a really economic method of synthesis has not been published. 3,4,6-Trichloropicolinic acid ("3,4,6-T") is a new compound (m.p. 128° C.) (not discovered by the present inventors). Due to the high reactivity of the 4-chlorine in polychloropyridine compounds, it has been very difficult to devise a practical method of making 3,4,6-T. The only method known to have previously been found gives a very poor yield of the compound (and does not involve $=$C—Cl reduction).

OBJECTS OF THE INVENTION

The primary object of the invention is to provide an efficient, economic method for the manufacture of 3,6-dichloropicolinic acid.

An additional object is to utilize 3,4,5,6-tetrachloropicolinic acid as a starting material for the preparation of 3,6-D or mixtures thereof with 3,4,6- and 3,5,6-trichloropicolinic acid.

Another object is to accomplish the foregoing objects by electrolytic reduction.

It is a particular object to provide a method for electrolytic reduction of a tri- or tetrachloropicolinic acid without resort to organic solvents, even though the acid has a low solubility in aqueous media.

A more specific object is to provide a method of electrolytically reducing tetrachloropicolinic acid, 3,4,6-trichloropicolinic acid or 3,5,6-trichloropicolinic acid, wherein an undivided body of a solution of the acid in an aqueous base serves as both catholyte and anolyte.

Yet another object is to provide a process in which, in a single operation, tetrachloro-2-picolinic acid can be converted to essentially pure 3,6-D in yields of at least 90%.

A further object is to provide a practical method of producing 3,5,6-trichloropicolinic acid, together with minor amounts of the 3,4,6-isomer, from tetrachloro-2-picolinic acid.

Still other objects will be made apparent, by the following specifications and claims, to those skilled in the art.

SUMMARY OF THE INVENTION

It has now been discovered that a chlorine substituent in the 4- or 5- position of tetrachloro-, 3,4,6-trichloro or 3,5,6-trichloro-2-picolinic acid can be selectively replaced with a hydrogen by passing direct electrical current to a cathode from an anode through a basic aqueous solution of said picolinic acid, if said cathode has a surface layer of silver microcrystals formed by the electrolytic reduction of colloidal, hydrous, silver oxide particles in the presence of an aqueous base.

It has been found that the mixed trichloropicolinic acids product obtainable by reduction of the tet-acid consists predominantly (up to about 99 mole %) of one isomer—which is indicated by the evidence now available to be 3,5,6-T. The balance of this product is believed to be the 3,4,6-isomer.

It is not presently known how to modify the tet-acid reduction to increase the proportion of 3,4,6-T in the tri-acid mixture. However, separation and accumulation of 3,4,6-T, as even a very minor by-product in ongoing 3,6-D manufacture, constitutes an improvement over the only other method known of for making 3,4,6-T.

The reactions involved in the reduction of tet-acid to 3,6-D may be depicted as:

a. Neutralization

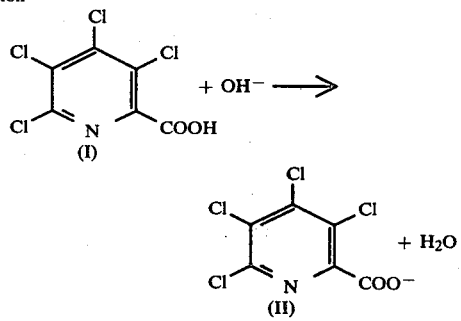

b. Cathode reactions

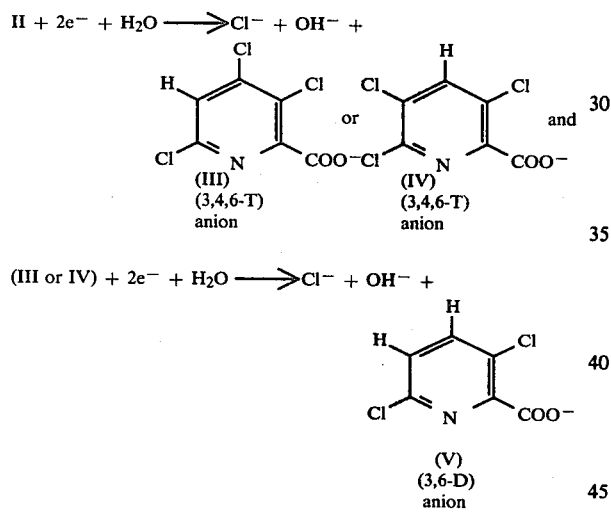

c. Anode reaction (for each —Cl replaced by an —H)

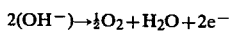

d. Overall reaction(s)

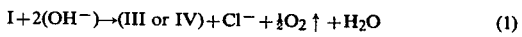 (1)

or

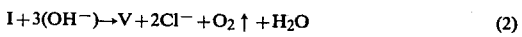 (2)

If 3,4,6-T and/or 3,5,6-T is used as a starting material, the reactions involved differ in that III or IV is formed directly by neutralization of the corresponding acid, rather than by reduction of tet-acid anions. The overall reaction is then depictable as:

(3,4,6-T or
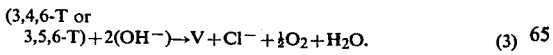 (3)

Thus, two chloride ions are formed and a total of three hydroxyl ions consumed for each tetrachloropicolinic acid molecule neutralized and reduced to the corresponding dichloropicolinate anion. If only one —Cl in the starting material (tet-acid, 3,4,6-T or 3,5,6-T) is replaced by H, one chloride ion is formed and two hydroxyl ions are consumed.

More specifically, the present invention may be defined as:

an electrolytic process for the coproduction of oxygen and polychloropicolinate anions of the structure

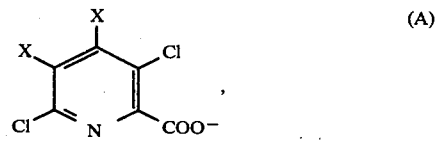

wherein one X is H and the other is H or Cl,
said process comprising,
providing a solution in water of a hydroxyl ion source-material and a polychloropicolinic acid of the structure

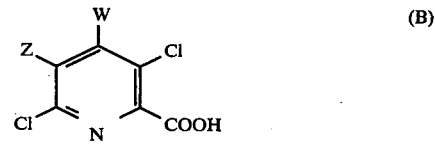

wherein both Z and W are Cl, or one is Cl and the other is H,
immersing a cathode in a body of said solution and, while agitatng said body, passing an electric current therethrough from an anode to the cathode,
said body of solution having a temperature within the range of from about 5° to about 60° C., a pH of at least 13, and containing at least 0.08 hydroxyl ions per chloride ion present therein,
said cathode comprising a shaped, electrical conductor in intimate contact with a water and hydroxyl ion-containing, immobilized, metastable layer of aggregated silver microcrystals formed by electrolytic reduction of colloidal, hydrous, silver oxide particles in the presence of water and hydroxyl ions, the cathode having a potential, relative to a saturated calomel reference electrode, of from about $-0.8$ to about $-1.8$ volts, and
said anode having a positive potential, relative to the cathode, such that the density of said current is from about 0.005 to about 0.085 amperes per $cm^2$ of projected cathode surface,
thereby forming anions of said polychloropicolinic acid (A) at said cathode and oxygen at said anode.

The use of a porous barrier between the catholyte and anolyte is not required and a single, stirred body of solution can function as both catholyte and anolyte.

In a less preferred embodiment of the invention,
a. the reduction mixture is a slurry of undissolved tetrachloropicolinic acid particles in a saturated solution of the acid in an aqueous alkali metal hydroxide.
b. initially, all of said acid (as such or as a salt) to be charged, and all of the hydroxide to be charged, is present in the slurry,
c. initially, the number of moles of said acid and salt per equivalent of hydroxyl is within the range of from about 0.1 to about 0.2 and d. the electrolysis is continued until at least 90% of the acid charged to the reaction has been converted to the corresponding base salt of 3,6-D.

In a more preferred method of practising the invention, the tri- or tetrachloropicolinic acid and/or a base is added during the course of the reduction.

Graphite is the preferred anode material in all variants of the present invention.

Also considered to be within the ambit of the present invention is an electrolytic cell in which the cathode is as specified above and is immersed in a catholyte comprising a solution of 3,4,6- or 3,5,6-trichloropicolinic acid and/or 3,4,5,6-tetrachloropicolinic acid in an aqueous base.

DETAILED DESCRIPTION

It is critical to the successful practice of the present invention that the cathode used be an active silver cathode, as above defined and as disclosed and claimed in said co-pending application, Ser. No. 029,600. Such cathodes and their preparation will now be described.

The essential physical-chemical nature of the metastable silver layer depends on its being formed in the presence of and continuing to include hydrated hydroxyl ions.

In a first form of the cathode, the active silver layer is adhered to a surface of the shaped conductor. In a second form, the active layer is a body of silver powder constrained within a liquid-permeable bag or envelope and the conductor either is surrounded (at least partially) by the powder or constitutes the envelope which "surrounds" (contains) the powder. In both forms, the conductor preferably consists of or is clad with silver, i.e., is a silver monolith or is a composite conductor comprising a conductive core sheathed with silver.

In the first form of the cathode, the microscopic topography of the active surface layer can vary (according to details of substrate character and the silver oxide reduction procedure). For example, the silver microcrystals may aggregate by packing closely together to form a plurality of mono- and polypartite "bumps" or dendrites protruding from and contiguous with a surface portion of the conductor or, pack loosely to form discrete particles which cohere with each other and adhere to the surface as a porous or "spongy" blanket which conforms to the substrate topography.

In the second form of the cathode, the silver particles initially formed (by reduction of the silver oxide particles) are in direct contact with the conductor and function as part of the conductor for the formation of the next layer of particles, and so on. Similarly, contact between the conductor and the powder particles not in direct contact with it is by electrical conduction through the intervening silver particles.

The silver oxide particles from which the active silver layer is derived can be formed in the immediate vicinity of the conductor, as by anodizing a silver conductor, or may be formed elsewhere and transported to it in the catholyte—as by stirring.

If at least the portion of the conductor surface at which the silver oxide particles are to be reduced is defined by an outer layer of silver, the oxide may be generated in situ by anodization of the silver. Thus, monolithic silver or silver-clad composite conductors are particularly convenient in affording electrodes which can be activated (or reactivated) in place in the cell to be used for carrying out a reduction.

Accordingly, cathodes comprising silver or silver-clad conductors are preferred. Such conductors may be of any configuration—such as a screen, plate, rod, etc., which is suitable for their intended function and which permits ready access of liquid to the silver surface at which the oxide reduction must proceed.

The presence of noble metals other than silver in the active surface layer has not been found beneficial and base metals (nickel and copper, most notably) definitely lower the activity of the cathode. Accordingly, it is highly desirable to minimize the content of metal ions other than silver in the reduction medium around the conductor (or cathode) when high 3,6-D yields are desired.

It then follows that, for maximum cathode activity, the conductor either should not be subjected to anodization or should consist of silver or a material which will not provide any substantial amount of ions (or reducible oxidation products) of other metals under the contemplated anodization conditions. (Analytically pure silver is not required but is of course preferred.)

The outer (or substrate) silver layer in a composite conductor comprising the same may be formed in any suitable manner, such as, for example, by electroplating silver on an electroconductive "core" or underbody. Since it is desirable for this layer to have a high surface area, the underbody surface on which the silver layer is formed does not have to be—and preferably is not—smooth. Similarly, a method of depositing the outer layer which favors columnar or dendritic growth or otherwise results in a high surface area—but not in lateral discontinuities in the silver in immediate contact with the underbody—is preferred.

In one variant of the cathode, the type of active overlayer which consists of protrusions contiguous with the silver substrate layer may in turn serve as a once-removed substrate layer which can be induced, by periodic polarity reversals, to cover itself with a conforming, porous blanket of cohered silver particles, thereby providing an outermost portion of the overlayer which has a still higher surface area structure of a character more like that of a "molecular sieve".

If the conductor is not to be subjected to anodization, it may consist of any otherwise inert, electroconductive material to which the silver microcrystals (as such or as particulate aggregates thereof) will adhere sufficiently well not to be swept off by a stirred catholyte. This includes nickel, stainless steel and—at least in principle—copper and graphite. Similarly, if such a conductor is first clad with a substantial thickness, of silver, it then becomes a composite conductor which may be activated by anodization.

As noted above, the colloidal silver oxide particles can be preformed and then introduced to the catholyte or can be formed in the catholyte—optionally, in the layer of catholyte in immediate contact with the silver base layer.

A convenient method of forming the oxide in a catholyte comprising water and hydroxyl ions is simply to add a small amount of a water-soluble silver salt, such as silver nitrate, with sufficient agitation to keep the resultant colloidal, hydrous, silver oxide particles well dispersed. Preferably, the salt is added as a dilute solution in water. Once formed, the oxide particles contact and are reduced at the negatively-charged cathode surface (the surface of the conductor) to build up the microcrystalline silver overlayer, i.e., to activate the cathode.

Formation of an active overlayer consisting of a non-adhered silver powder is facilitated by using an envelope to effectively immobilize the silver oxide precursor particles in close contact with each other and/or the conductor; the reduction then more closely approximates an all-at-once production of the microcrystals and growth of earlier formed nuclei (crystals) by accretion of later formed microcrystals is minimized.

The envelope may or may not be electroconductive, but must be readily permeable to the aqueous phase of the catholyte. If it is conductive, it may also function as the conductor. If it is not, a separate shaped conductive member (such as a wire or patch of metal screening, for example) which can be inserted or embedded in the body of oxide particles to be reduced, will be required. The envelope may be foraminous (as a fine meshed gauze or screen, for example) or microporous (as a TEFLON ® or polyethylene diaphragm having a porosity and average pore size such as to permit a practical rate of transport through it of the aqueous tetrachloropicolinic acid salt solution).

The envelope should be so formed about the body of silver oxide particles (to be reduced), as by flattening, crimping or stretching, as to exert some compression on it, thereby ensuring better contact between the resultant silver powder particles.

If further activation (or reactivation) of the powder, by anodization, is not contemplated, the central conductor or conductive envelope can consist of a metal such as nickel, stainless steel or even copper, to which silver has less tendency to adhere, thereby further ensuring a high conversion of the silver oxide particles to unattached silver particles.

In an alternative method of activation ("anodization") the silver which makes up the active overlayer is derived from the (silver) substrate layer itself. The unactivated electrode is dipped or immersed in a catholyte containing water and hydroxyl ions and is anodized (anodically polarized), thereby converting some of the silver in the base layer surface to colloidal silver oxide and roughening (corroding) the surface at the same time. The polarity of the electrode is then reversed and the oxide electrolytically converted to protrusions or particles of microcrystalline silver (without re-smoothing the surface it is adhered to). Preferably, the polarity reversal is repeated several times at intervals of about 30 seconds. This same procedure can also be employed to reactivate a silver cathode which exhibits diminished activity.

Water plays an important, albeit not well understood, role in the formation and retention of the fine structure which is essential to the activity (and selectivity) of the metastable silver overlayer. Both water and hydroxyl ions (hydrated hydroxide ions, at least) must be included in the overlayer when it is formed—and until it is no longer to be utilized in a cathode. Once formed, the microcrystalline superstructure will collapse somewhat and its activity will be at least substantially diminished if its content of water is allowed to decrease below some minimum critical level. Whether or not this level corresponds to a monomolecular layer (over the entire fluid-accessible surface of the overlayer) is not known. Although the critical contents of water and base can readily be determined for any specific, reproducible cathode, this is not necessary if the cathode is simply kept immersed in an appropriate basic, aqueous medium. Preferably, the latter medium is simply that in which the electrode was immersed when it was "activated", or is an aqueous base in which the tetrachloro acid to be reduced will be dissolved.

The activation procedure is not adversely effected by the presence, with the required water and base, of polychloropicolinate anions. Accordingly, activation most conveniently is carried out simply as the first step in the reduction for which the cathode is employed. This is true for either of the two general activation methods discussed above, which will now be discussed in more detail.

In the activation method involving formation of the silver oxide particles in the catholyte, it is not necessary to establish a substantial silver content therein; silver contents of about 100 ppm (parts per million) are generally sufficient and contents substantially in excess of about 500 ppm are of no additional benefit and may actually be wasteful. The solution of the silver salt can be added to a preformed catholyte mixture or to the aqueous base component thereof before the tetrachloropicolinic acid is introduced. The requisite degree of agitation during the oxide deposition step is conveniently attained with magnetic stirring.

The silver oxide particles to be reduced in forming an active silver overlayer may be preformed in a separate container and then introduced to the catholyte—together with or separated from the aqueous medium in which they were formed. When the overlayer is to take the form of a silver powder, it is convenient to filter out the oxide particles and to transfer them (wet with aqueous base) to the envelope in which they will be reduced. The envelope can be formed from a flat sheet of gauze or other suitable material on which the oxide particles have been placed, or may be a preformed, porous container (such as a porous fluorocarbon elastomer bag, for example) in which the particles are lightly packed.

In the activation method involving anodization of a silver substrate, the current density is usually controlled so that the potential at the electrode surface rises, in a period of several minutes, from an initial value of, say, zero volts to a final value of at least $+0.3$ volts and preferably about $+0.6$ volts. It is not necessary to add any silver to the catholyte (or aqueous base) in this method.

It is known (*Electrochemical Reactions*, Charlot et al; pp. 298, 9; Elsevier Pub. Co., Amsterdam, N.Y., 1962) that the electrolyte oxidation of silver at progressively higher potentials in the presence of hydroxyl ions, results in the formation of not only $Ag_2O$ but also of higher oxides in which silver takes on nominal valences greater than one. The calculated positive (anode) potentials corresponding to formation of $Ag_2O_2$ and $Ag_2O_3$, in about 13 N KOH, are, respectively, about $+0.6$ and about $+0.8$ volts. A potential of about $+0.6$ volts is currently regarded as optimum for the in-situ preparation of silver oxide particles from which the active silver layer is to be prepared; however, potentials as high as $+0.8$ volts are not ruled out.

Reduction of the oxide deposit requires negative polarization of the cathode in both methods of activation. In the first method discussed above, the cathode potential is negative to start with and may range from about $-0.5$ to about $-2.0$ volts; preferably it is from about $-1.0$ to about $-1.5$ volts. In the second method, the polarization of the cathode is gradually reversed. That is, the cathode potential is gradually reduced from the value (about $+0.3$ to about $+0.6$ volts) attained in the oxidation step, to a value of about $-0.5$ volts or less (down to about −2.0 volts). In the first method, the current is relatively low in the early stage of oxide reduction. Thereafter, the current will rise to an essentially steady value, assuming a reducible material (polychloropicolinate anions) is present in the catholyte. However, in the second method, the current drops off from an initially higher level to a minimum, at which point (potential about −0.5 volts) the oxide reduction is complete. If the potential is lowered further, the current will then increase—again assuming a reducible material is present—to a value of about 1.5 amps (cathode potential about −1.0 to about −1.5 volts).

Before the cathode is activated by either method, it preferably is cleaned, as by immersing it in aqueous hydrochloric acid (1:1 water and c.HCl) for about ten minutes. Similarly, when a cathode which has been used as such for some time and is to be reactivated, it should first be cleaned in the same manner, to essentially remove any detrimental metals which may have plated out on it.

As an exception to the foregoing teachings with regard to deleterious effects of certain metal ions which tend to plate out on the cathode, some deactivation of the silver micro-crystal layer at the cathode surface is apparently desirable for the production of trichloropicolinic acids. The initial reduction of tet-acids to the trichloro-intermediates proceeds more readily than the further reduction to 3,6-D. By using a less active cathode, the selectivity of the reaction for the trichloro- compounds is increased.

Suitable anode materials for the practice of the present invention are those which are inert, i.e., do not detrimentally react with any of the catholyte components (or oxygen) to an intolerable extent. However, 3,6-D yields (based on tet-acid charged) of 90% or better have been attained only with anodes consisting essentially of graphite. This is apparently because decarboxylation ("Kolbe type" oxidation of polychloropyridine carboxylate anions) tends to occur at anodes consisting of other materials.

The composition of suitable catholytes (reduction mixtures) for the practice of the invention will now be discussed. The catholyte must comprise an aqueous phase containing both hydroxide ions and anions of the polychloropicolinic acid to be reduced. This phase may also include dissolved salts of 3,6-D and such by-products as may be formed in the course of the reduction.

Ordinarily, the hydroxide ions (and the required positive counter ions) will be provided by an alkali metal hydroxide. However, any otherwise suitable source of hydroxyl and counter (cat) ions may be employed. Sodium hydroxide is highly preferred as the hydroxyl ion source material (base, herein). Commercially available "pure" (mercury cell) 50% aqueous NaOH has been found quite satisfactory. For the production of 3,6-D, at least, it is highly preferred that the catholyte (the aqueous phase that is) comprise less than about 20 ppm, total, of base-metal ions, but reagent grade caustic is generally not required.

The catholyte may also include a second phase which comprises 3,4,6-T, 3,5,6-T or tet-acid and is dispersed or suspended in the aqueous phase. Preferably, neither this phase or the aqueous phase will contain any substantial proportion of other organic materials. However, dissolution of the un-neutralized polychloro-acid(s) in an organic solvent which is essentially immiscible with the aqueous phase but permits transfer of enough of the acid to the aqueous phase to keep the latter saturated with the acid salt to be reduced is considered feasible. This, of course, is with the proviso that an intractable emulsion does not result from inclusion of the solvent.

Similarly, the aqueous phase may include one or more dissolved organic solvents, of such character and in such amounts as not to deleteriously effect the cathode, the electrode reactions or product recovery to an intolerable extent. However, it is a distinct advantage of the present invention that conventional co-solvents—which are generally flammable and often toxic and/or prone to peroxide formation—are not required.

In the presently preferred mode of operation, the substrate acid (the acid to be reduced) is added incrementally to the catholyte as a powdered solid. Advantageously, this solid is pre-slurried with a portion of the catholyte (or with an aqueous base) before being added to the cell. It has been found that undissolved tet-acid particles, when wet with the aqueous phase, tend to aggregate as relatively large lumps which are then difficult to break up. Also, the particles tend to form a "foam" (which is unresponsive to defoaming agents) when contacted by the gases evolved in the reduction. Both of these difficulties are minimized by slow addition of the acid, ideally at a rate about equal to the rate at which the dissolved acid salt is converted in the reduction.

For the preparation of 3,6-D in high yields, it is critically important that the pH of the aqueous phase of the catholyte be kept at a level of about 13 or higher throughout the reaction. It is also essential in this regard that the number ratio of hydroxyl to chloride ions therein not be allowed to fall substantially below 0.6 ($OH^-/Cl^-$ weight ratio 0.3). Otherwise, appreciable amounts of chloride oxidation products (hypochlorite, for example) and decarboxylated chloropyridines may form at the anode.

The foregoing pH and $OH^-/Cl^-$ conditions are considered similarly desirable when the process of the invention is used to make 3,4,6-T and 3,5,6-T from the tet-acid.

Preferably the $OH^-$ to $Cl^-$ equivalent (or number) ratio is kept at or above a level of 1.

Ordinarily, the lowest $OH^-/Cl^-$ ratio at which reduction will be carried out will occur just prior to the end of the reduction, i.e., when the most $OH^-$ has been consumed and the most $Cl^-$ produced. At any stage of reaction, the minimum value to which the ratio can fall will be that attained if the reduction is allowed to proceed until all of the tri- and/or tetrachloro-acids charged have been reduced to 3,6-D. This minimum value is equal to $(a-3b-2c) \div (2b+c+d)$, where a is the gram ions of $OH^-$ charged, b is the gram moles of tet-acid, charged, c is the gram moles of 3,4,6-T and/or 3,5,6-T charged and d is the gram ions of $Cl^-$ charged (initially present). If c and d are nil, the foregoing quotient reduces to $(a-3b) \div (2b)$. If b and d are nil, the expression instead reduces to $(a-2c) \div c$.

The assumption that no side reactions occur is implicit in the way the quotient is defined and the value calculated for it is therefore a theoretical minimum which will seldom be realized. However, in most instances, the actual lowest $OH^-/Cl^-$ ratio attained will not greatly differ from the theoretical minimum. The latter quantity thus may be used as a practical criterion of the relative amounts of base and substrate acid(s) employed in a given reduction.

Thus, when tet-acid is to be converted to 3,6-D in high yield, the gram moles of tet-acid which can be charged per g. ion of OH⁻ charged, without causing the OH⁻ to Cl⁻ ratio to drop substantially below 0.6, is found by setting 0.6 equal to $(1-3b) \div 2b$ and solving for b; i.e., b=~0.24. Similarly, if 3,5,6-T is to be converted to 3,6-D and an OH⁻/Cl⁻ ratio of at least 0.6 maintained, $0.6=(1-2c) \div c$ and c=0.38; i.e., not more than 0.38 gram moles of 3,5,6-T should be charged per gram ion of OH⁻ charged.

So far, reduction of tet-acid to 3,4,6-T, without co-formation of 3,5,6-T and 3,6-D in substantial proportions, has not been achieved. The general expression for the theoretical final OH⁻/Cl⁻ ratio in this case is $(a-b(3x+2y+z)) \div (b(2x+y)+d)$, where a, b and d are as above defined, x and y are, respectively, the mole fractions of the tet-acid converted to 3,6-D, and to "tri-acids" and z is the mole fraction of tet-acid unconverted. Thus, in a typical reaction, 1 gram mole of tet-acid produces a mixture for which z=0.1, x=0.5 and y=0.4. If a nil original Cl⁻ content and a theoretical final OH⁻/Cl⁻ ratio of 0.8 are assumed, then a, the amount of OH⁻ required to be charged, is found from the equality, $0.8=(a-1(1.5+0.8+0.1)) \div (1(1+0.4))$-$=(a-2.4) \div 1.4$, to be at least 3.52 gram ions (or 3.52 gram moles of an alkali metal hydroxide, for example), i.e., the mole ratio of tet-acid to the hydroxide should not exceed 1/3.52 or 0.284).

It is apparent from Example 8c, herein, that even at a theoretical minimum (or final) OH⁻/Cl⁻ ratio as low as 0.08, tet-acid can be converted to 3,6-D in about 77% yield. At the other extreme, if no chloride ions are initially present, the OH⁻/Cl⁻ ratio at onset of the reduction is infinite; thus, there is no upper limit to this ratio.

When the hydroxyl ion source-material is NaOH (and tet-acid is the only polychloropicolinic acid substrate charged), the overall weight ratio of tet-acid to NaOH charged should be within the range of from about 0.5 to about 2.1, but preferably is from about 0.65 to about 1.3. The corresponding mole ratio ranges are from about 0.075 to about 0.32 and (preferably) from about 0.1 to about 0.2; the latter ranges apply to alkali metal hydroxides in general.

The concentration of the hydroxyl-ion source material in the catholyte can range from that required as a minimum for a pH of 13 to that at which the solubility of the tet-acid salt of the base employed becomes impractically low. In the case of sodium hydroxide, the latter range is from about 0.4 wt. % to about 15 wt. %. The preferred range for NaOH is from about 5 to about 7 wt. % (about 2.1 to about 3 wt. % OH⁻). In terms of moles, the latter ranges, respectively, are from about 0.1 to about 3.75 and (preferably) from about 1.25 to about 1.75 gram moles of NaOH per 1000 grams of catholyte ($H_2O$, NaOH, substrate acid). Approximately the same ranges are considered suitable for other alkali metal hydroxides.

The relative amount of 3,4,6-T, 3,5,6-T and/or tet-acid which can be present in the catholyte as undissolved materials should not exceed about 12 weight percent of the catholyte; the slurry is undesirably viscous at higher levels. The tri- and tet-acid salts (such as the sodium salts, for example) are soluble in strong aqueous bases (10% NaOH, for example) only to the extent of a few percent by weight, so the total content of unconverted acids (dissolved and undissolved will generally not exceed about 15 wt. %. Of course, more tri- or tet-acid may be introduced as the reaction proceeds, so long as this does not result in an OH⁻/Cl⁻ number ratio of less than about 0.08. Likewise, more hydroxide-ion source material may also be added, but the catholyte must retain sufficient fluidity and solvent ability (for the acid salt) to ensure stirrability and an adequate reaction rate.

When the entire amount of polychloro-acid to be charged is not initially present in the catholyte, the balance may be added as the free acid or as a preformed salt of the base employed, together with as much extra base as may be required to ensure that the OH⁻/Cl⁻ ratio does not drop too low.

It has been found that the 4-chlorine substituent in the tet-acid (or in 3,4,6-T) tends to undergo base hydrolysis, even at room temperature. Consequently, a basic, aqueous solution of such a polychloropicolinic acid which is to be electrolyzed should either be freshly prepared or kept cold.

Suitable temperatures for the electrolysis generally range from about 5° to about 60° C. At temperatures above 50°, side reactions (such as hydrolysis) occur to a sufficient extent to seriously effect yields, complicate 3,6-D and $O_2$ recovery and present by-product disposal problems, and at temperatures below 10° C., tet-acid solubility is undesirably low. The preferred temperature range is from about 20° to about 40° C. and the most preferred range is from about 34° to about 36° C.

Suitable contact times, for tet-acid to 3,6-D conversions of 90% or better, range from about 12 hours (at about 20° C.) to about 3½ hours (at about 40° C.). Times in excess of 10 hours tend to result in some over-reduction and/or side reactions (particularly at temperatures above 30° C.).

The rate of 3,4,6-T and 3,5,6-T reduction of course drops considerably in the later stages of the reaction, so suitable contact times when the tri-acid(s) are employed as a pre-formed starting material are not greatly shortened. However, if production of 3,4,6-T and 3,5,6-T (and 3,6-D) from tet-acid is desired, substantially shorter contact times are appropriate. Thus, at a cathode potential of −1.3 volts and a temperature of about 25°-28° C., the product mixture may (depending on cathode activity) comprise up to 55 mole % of trichloro acids, about 40 mole % of 3,6-D and about 5 mole % of tet-acid, after 2 hours contact. After about 3-3.5 hours contact, approximately equal amounts of the "tri-acids" and 3,6-D, and essentially no tet-acid, will be present.

The electrical requirements for the electrolysis are as follows.

The cathode potential, relative to a standard, saturated calomel reference electrode, should be within the range of from about −0.8 to about −1.8 volts; this potential preferably is from about −1.2 to about −1.5 volts for 3,6-D preparation and a potential of from about −1.3 to about −1.4 volts appears to be optimal. For the preparation of 3,4,6-T and 3,5,6-T (by tet-acid reduction), a potential of from about −0.8 to about −1.2 volts appears to be better; note Example 11 herein.

(At a cathode potential of −1.3 volts, enough hydrogen is produced (at the cathode; by electrolysis of water) to account for at least 5% of the cell current. At cathode potentials more negative than about −1.5 volts, hydrogen evolution is pronounced and can account for over 10% of the cell current.)

The current density, in amperes per $cm^2$ of projected cathode surface (face nearest to anode) should be within the range of from about 0.005 to about 0.085; 0.08 appears to be optimal, i.e., results in a high level of tet-acid (or tri-acid) conversion without substantial anodic oxidation of the reduction products thereof.

The cell voltage (potential difference between the anode and cathode) is determined (for a given current flow) by the resistance through the cell and of course is kept as low as is practical. However, this potential will usually be about 2 volts.

Current efficiencies of better than 90% have been attained in the practice of the present invention on a laboratory scale. On a pilot plant scale, efficiencies of about 70 to 80% have, so far, been more typical.

If it is elected to employ a porous barrier, such as a diaphragm or porous ceramic cup, between the catholyte and anolyte, the anolyte may consist simply of an aqueous base—such as, for example, 10% aq. NaOH. It is highly preferred not to use a barrier, i.e., to immerse both anode and cathode in a single, undivided, agitated body of a basic aqueous solution of the tet-acid salt.

It is essential to efficient operation of the electrolysis process that the catholyte (and anolyte) be sufficiently agitated, as by magnetic stirring, for example. High shear or intense stirring is not necessary but the degree of agitation should be such that no volume element of the solution differs in polychloropicolinate or hydroxyl content from the average for the solution as a whole by more than a few percent.

Suitable cells for the practice of the invention comprise an active silver cathode, as defined earlier herein, an anode which preferably consists of graphite, a standard reference electrode (such as a saturated calomel electrode in a Luggin capillary) positioned so as to just touch the cathode, a stirring means such as a magnet bar, means for collecting (separately) the gases evolved at the cathode and anode, means—such as a potentiostat—for indicating and controlling the cathode and cell voltages, and a pair of electrical leads for connection to a source of D.C. All portions of the cell which come in contact with the catholyte/anolyte of course should be resistant to basic, aqueous salt solutions, or at least should be incapable of providing thereto metal ions which will plate out on the cathode. Materials which have been found or are considered suitable as the container component of the cell are glass, silver-plated metals, Lucite, graphite and other materials commoly employed in chlor-alkali electrolytic cells.

It is generally preferred to use a cylindrical cathode (such as a cylindrical, silver, 20 mesh screen, for example) around a central anode which may or may not be of conforming shape and is spaced about 1-2.5 cm from the cathode. However, the container, if it consists of a conductive material, such as graphite, for example, may also function as an anode which surrounds the cathode. Similarly, a silver or silver-clad, conductive container can also function as the cathode. (Of course, appropriate safety precautions—such as insulation or grounding—should be taken if the container is conductive.

Preferably, the cell is provided with a polarity reversing means (for activation or reactivation of the cathode) and a temperature control means, such as a thermostatically-controlled water bath.

Recovery of the gases evolved at the electrodes is readily accomplished in a conventional manner. Work-up of the reaction mixture (catholyte/anolyte) for 3,6-D recovery is simple and straight forward. The 3,6-D salt is precipitated as the free 3,6-D acid by acidification to a pH of about 0.5, as with c. aq. HCl, for example, and is then separated by filtration or by dissolution in an organic solvent (dichloromethane, for example) which is essentially immiscible with water. The crude 3,6-D may be recovered in amounts equivalent to 90 to 99% of the theoretical yield and in a purity of up to about 98%, by evaporation of the dichloromethane. The 3,4,6- and 3,5,6-trichloro-2-picolinic acids, can be removed by recrystallization of the crude product from an aqueous solvent (such as water, brines or aqueous alcohol, for example) freed of solvent and recycled to the reduction. In those applications where inclusion of the trichloroacids is not a problem, the crude 3,6-D may be used "as is". It is possible to obtain a crude 3,6-D product that contains very little of the trichloroacids by prolonging the electrolysis beyond the point at which the reaction rate becomes so low that the current efficiency drops off substantially.

When the process is operated for production of trichloroacids (and 3,6-D), the mixed trichloroacids may be recovered from the 3,6-D mother liquor as a second or third crop. The mixture can then be resolved by known separatory techniques, such as preparative chromatography. 3,4,6- and 3,5,6-T melt at 128° C. and 144° C., respectively.

The active silver layer on the cathode may be modified (partially deactivated) by deliberately occluding a portion (preferably a minor proportion, i.e., less than 50%) of its surface with base metal deposits. This may be done, for example, by immersing the activated electrode in an aqueous base containing base metal cations and cathodically polarizing it.

The following examples are for purposes of illustration and are not to be construed as limiting the present invention in a manner inconsistent with the claims appended herewith.

EXAMPLES

I. Preparation of Active Silver Cathodes Suitable for Employment in the Process of the Invention. (Not Illustrative of that Process Itself.)

Example 1 —Cathodes comprising an active silver layer adhered to a silver foil (a) A rectangular (0.005"×2"×3") piece of smooth silver foil is immersed in 10% aqueous caustic containing several hundred parts per million of colloidal silver oxide (formed upon addition of a dilute silver nitrate solution to the caustic). A counter electrode is also immersed in the caustic and the silver foil is cathodically polarized at a potential (relative to a saturated calomel electrode) of about −1.5 volts and the potential difference between it and the anode is adjusted to give a current of about 1.5 amperes. Reduction of silver oxide at the cathode surface is allowed to proceed for about half a minute.

A small portion of the silverized foil is cut off, air-dried and observed to have a rough matte-white appearance. The remainder of the foil is kept immersed in the catholyte and is subjected (by means of a throw switch) to a series of four polarity reversals at thirty second intervals. The resulting "anodized" foil is removed from the cell, air-dried and found to have the appearance of dark brown to black foam.

Both portions of the foil (on the side facing the anode) are examined by scanning electron microscopy (SEM), X-ray dispersive fluorescence and electron diffraction (reflection). The other layer of the matte-white (unanodized) foil is "seen" to be a deposit of closely spaced, generally hemi-spherical "bumps" which are contiguous with the underlying foil, have maximum dimensions of up to about 25 microns and are composed of densely packed, face-centered, cubic silver microcrystals (about 0.05 to 1 micron in "diameter"), the bumps being laterally connected at their bases and in some instances "fused" together to form polypartite bumps having maximum dimensions of from about 30 to about 50 microns.

The microscopic topography of the anodized foil is essentially the same, but the bumps are coated with a relatively thin layer of a silver deposit having the appearance of a "moss" at 100 magnifications. The moss is found to consist of loosely packed, face-centered, cubic silver microcrystals having a narrow-size distribution around an average maximum dimension of about 0.05 microns. At a magnification of 10,000×, the "moss" looks like sponge cake and may be described as having a "spongy" character.

(b) A silver layer is electroplated from an ammoniacal solution of silver nitrate on a nickel substrate, peeled off as a foil and sampled for examination by SEM, X-ray fluorescence and electron diffraction. The surface of the foil which has been exposed to the silver solution, washed and air dried, is matte-white in appearance and, at 2000 magnifications, is "seen" to have a surface layer of generally irregular, flattened "bumps" which have maximum dimensions of up to about 25 microns and are so embossed with flattened, irregularly shaped, microprotrusions as to have an etched appearance. Some of the bumps consist of portions of well defined, individual crystallites having maximum dimensions of up to about 6–10 microns. At a magnification of 50,000×, all discrete surface areas are relatively smooth in appearance.

The remainder of the foil is anodized in the preceding manner (a, above), washed, air-dried and examined by SEM, etc. It has a brown color and is found to be coated with a layer of generally dendritic protrusions, of which the more elongate are joined at their bases into clusters—in some instances being largely fused together. The individual dendrites are seen (at 2000×) to have "diameters" of about 5–10 microns and lengths of about 10–20 microns. These dendrites are composed of closely packed, face-centered, cubic silver microcrystals and the dendrite surfaces are seen (at 50,000×) to be defined by an outermost, porous layer of discrete but cohered, generally spherical to oblate, silver crystalites varying in size (maximum dimension) from about 0.05 to 0.07 microns.

(c) A piece of clean silver foil, essentially the same as that employed in part (a) of this example, is examined by SEM and is "seen" to have a surface resembling (at 500×) that of a paper towel (at 1×). At 10,000×, this surface shows a pattern of grain boundaries resembling incipient cracks between slight elevations in an otherwise flat body of mud.

The foil is immersed in 6% aqueous NaOH in which a counter electrode is also immersed and is anodized, as follows, for 3 minutes. The potential of the foil (relative to a saturated calomel electrode) is raised from 0 to +0.3 volts in about 30 seconds and then, gradually, to +0.6 volts during the following 2.5 minutes. The potential is then gradually reduced to 0, and finally to −1.3 volts.

The anodized foil, together with enough of the cell liquor to keep it covered, is then sealed in a glass container and submitted for prompt examination by SEM, X-ray dispersive fluorescence and electron diffraction.

A sample of the wet, anodized foil is cut off, glued wet to an SEM stub and immediately placed in the SEM column for imaging. Another sample is cut off and alowed to air dry 24 hours before being scanned. The remainder of the anodized foil is allowed to age 24 hours in the cell liquor and then scanned.

The freshly activated (wet) foil sample is "seen", at 12,500×, to be covered with an adherent, highly porous blanket of cohered, angular particles consisting predominantly of more than one (face centered, cubic) silver microcrystal each and ranging in size (maximum dimension) from about 120 Å (0.012 micron) to about 0.5 micron.

The structure of the blanket on the air-dried sample is found to be uniformly more condensed and to comprise a high proportion of relatively large (0.2–0.5 microns maximum dimension) particles readily recognized (at 25,000×) as generally cubical in shape.

The coating on the wet-aged foil sample is found to have condensed less uniformly, having pulled apart laterally in some places to expose underlying, essentially smooth surface areas. The proportion of generally cubical particles is lower and they are less well defined and, on the average, smaller (up to about 0.3 microns, maximum dimension).

EXAMPLE 2—Silver Powder Cathode

An amount of hydrous silver oxide(s) precipitate containing 2 grams of silver is formed by adding a dilute (2%) aqueous silver nitrate solution to a stirred body of 5% aqueous NaOH. The precipitate is filtered out and transferred (wet) to a flat, appropriately cut piece of 100 mesh, stainless steel screen, which is then folded and edge-crimped to form an electrically conductive, 5 cm×7.5 cm envelope containing—and restraining—the oxide precipitate. The envelope is then immersed in 5% aqueous NaOH, in which a graphite counter electrode is also immersed, and cathodically polarized to reduce the oxide(s) to powdered silver. The current gradually drops off, over a period of 15 minutes, from an initial value of about 4 amperes to a then steady value of about 0.5 amperes (at an average cathode potential of about −1.5 volts), and the reduction is essentially complete.

A sample of the resulting silver powder is removed, together with some of the cell liquor, and submitted for immediate SEM (etc.) examination without being dried. The powder particles are found to be essentially the same as those making up the coating on the freshly activated, wet foil sample in part (c) of Example 1.

II. Laboratory Scale Reductions of Tetrachloro-2-picolinic Acid (Tet-acid) to 3,6-dichloropicolinic Acid (3,6-D); Cathode Activated in-situ.

Example 3—(Cell A)

To a 300 ml glass beaker, containing a magnetic stirring bar and mounted on a magnetic stirrer, is charged a solution of 15 grams of reagent grade NaOH pellets in 150 ml of distilled water. A planar, 5 cm×7.5 cm, 20 mesh, silver screen cathode, a saturated calomel reference electrode and a planar, 5 cm×7.5 cm×2 mm graphite anode plate (spaced 1 cm from the cathode) are immersed in the upper portion of the solution. The stirrer is turned on, a source of direct current is connected across the cathode and anode and 3 ml of water containing 60 milligrams of $AgNO_3$ is added to the stirring slurry. The potential of the cathode, relative to the reference electrode, is held at −1.3 volts and the cell potential is set (@~2 volts) for an initial current of 3 amperes. 10 grams of tet-acid is added over an interval of 30 minutes. Over a total period of 4.5 hours (at about 25° C.) the current falls, exponentially, to less than 0.3 amperes and the reduction is terminated. 6.8 grams of white solids are recovered by acidification (28 ml c. HCl) and extraction of the electrolysis solution with CH$_2$Cl$_2$ and evaporation of the extract. By infrared and gas chromatographic analyses, the crude product is found to have a 3,6-D content of 92.2 wt. %.

EXAMPLE 4

Example 3 is essentially repeated, except that no silver nitrate is added and the cathode is activated by several polarity reversals of a few seconds each (stirrer off). 7.2 grams of crude product (97.9% of theory), having a 3,6-D content of 91 wt. %, is recovered.

EXAMPLE 5

Example 4 is essentially repeated, except that when about 95% of the initially charged tet-acid has been converted, another 10 grams of tet-acid and 3 grams of NaOH are added and the electrolysis is continued for a total of 9 hours. 14.6 grams (99.3% of theoretical yield) of crude product having a 3,6-D content of 91.4 wt. % is obtained.

The overall mole ratio of tet-acid to NaOH for this run is 0.17 and the final OH$^-$/Cl$^-$ ratio (assuming 3,6-D as the only reaction product) is approximately $(18/40-(3\times0.914\times20/261) \div (2\times0.914\times20/261) = 1.7$. The final wt. % of NaOH in the reaction mixture is about $[18-40(3\times0.914\times20/261)]\times100/188 = 5.1\%$. (If the weights of H$_2$ and O$_2$ evolved in the course of the reaction were taken into account, this figure would be somewhat higher.)

Example 6

A series of six experimental reductions (a–f) is carried out, using a cylindrical, 20-mesh silver screen cathode, which is activated by anodization, i.e., essentially in the manner of Example 4 above. The cathode is vertically disposed around a planar, 5 cm×7.5 cm×2 mm graphite anode plate and has a diameter of about 7 cm. The D.C. voltage source employed is a Model 317 Potentiostat (Princeton Applied Research) and the cell (either a 300 cc or 600 cc glass beaker, depending on the volume of the reaction mixture) is partially immersed in thermostatically controlled water bath. A saturated calomel reference electrode in a Luggin capillary is positioned so that the tip of the capillary just touches the cathode. Stirring is provided by a magnetic stirrer (under the water bath) and a magnetic bar.

The amount of reactants employed, the reaction conditions and durations and the yields and purities of the crude 3,6-D product obtained (by acidification, extraction and evaporation) are given in Table I following.

It should be noted that the "final" OH$^-$/Cl$^-$ ratios given in the table are the theoretical minimum ratios calculated by assuming 100% conversion of the tet-acid to 3,6-D.

TABLE I

REDUCTIONS OF TET-ACID AT SILVER SCREEN CATHODE

| Run | H$_2$O Vol. ml | NaOH Wt. Grams | NaOH Wt. % | Tet-Acid Wt. Grams | Tet-Acid Wt. % | Initial Mole Ratio Tet-Acid/NaOH | Final No. Ratio OH$^-$/Cl$^-$ | Cathode Pot'l Volts | Current Amps Start | Current Amps End | Reac. Temp. °C | Reac. Time Hrs. | Product % Theor. Yield | Product 3,6-D Content Wt. % |
|---|---|---|---|---|---|---|---|---|---|---|---|---|---|---|
| 6a[3] | 150 | 15 | 8.57 | 10 | 5.71 | 0.102 | 3.40 | −1.3 | 2.0 | 0.2 | 30 | 6 | 92 | 92 |
| b | 150 | 12 | 6.98 | 10 | 5.81 | 0.128 | 2.42 | −1.3 | 2.0 | 0.2 | 30 | 6 | 92 | 92 |
| c | 150 | 5 | 3.03 | 10 | 6.06 | 0.307 | 0.13 | −1.3 | 2.0 | — | 30 | | Reac. stopped at 50% conversion[1] | |
| d | 300 | 18 | 5.33 | 20 | 5.92 | 0.170 | 1.44 | −1.35 to −1.3 | 1.6 | 0.3 | 26 to 50 | — | 99 | 91 |
| e | 200 | 20 | 8.33 | 20 | 8.33 | 0.153 | 1.76 | −1.6 | 3.5 | — | 55 to 25 | 11 | 90 Reac. stopped | 97 |
| f | 150 | 12 | 6.98 | 10 | 5.81 | 0.128 | 2.42 | −1.6 to −1.8 | 4.0 | 4.0 | 30 | 4 | @ 50% conv.[2] | |

Notes:
[1]CO$_3^-$ and OCl$^-$ formed.
[2]Excessive H$_2$ evolution (at cathode).
[3]Current Efficiency about 90%.

Example 7

A series of three reductions (a–c) of tet-acid is carried out essentially as in Example 6, except that the silver screen employed as a cathode is silver plated (prior to being activated) by cathodic polarization in an ammoniacal AgNO$_3$ solution.

Three additional reductions (d–f) are carried out in the same manner except that the cathodes employed are formed of: (a) and (b), a silver plated monel screen, and (c), a silver plated nickel screen.

Collection and analysis of the gases evolved at the electrodes during these runs shows that the rate of oxygen evolution (at the cathode) is close to theory for the overall reaction, as represented earlier herein and is from about 10 to 15 times the rate of hydrogen evolution (at the anode).

These six experiments are summarized in Table II, following.

TABLE II
REDUCTIONS OF TET-ACID AT SILVER PLATED SILVER SCREEN CATHODE

| Run | H$_2$O Vol. ml | NaOH Wt. Grams | NaOH Wt. % | Tet-Acid Wt. Grams | Tet-Acid Wt. % | Initial Mole Ratio Tet-Acid NaOH | No. Ratio OH$^-$/Cl$^-$ | Cathode Pot'l Volts | Final[1] Current Amps Start | Final[1] Current Amps End | Temp. °C. | Reac. Time Hrs. | Product % Theor. Yield | Product 3,6-D Content Wt. % |
|---|---|---|---|---|---|---|---|---|---|---|---|---|---|---|
| 7a | 200 | 24 | 9.84 | 20 | 8.20 | 0.128 | 2.42 | −1.3 | 3.5 | 0.5 | 30 | 4 | 95 | 98 |
| b | 300 | 24 | 6.98 | 20 | 5.81 | 0.128 | 2.42 | −1.3 | 2.0 | 0.5 | 23 | — | 98 | 99 |
| c | 300 | 36 | 9.84 | 30 | 8.20 | 0.128 | 2.42 | −1.3 | 2.0 | 0.5 | 23 | 12 | 98 | 98 |
| d | 150 | 12 | 6.98 | 10 | 5.81 | 0.128 | 2.42 | −1.3 | 1.0 | 0.2 | 27 | 7 | 90 | 99 |
| e | 100 | 6 | 5.40 | 5 | 4.50 | 0.128 | 2.42 | −1.4 | 2.0 | 0.3 | 23 | 6 | 95 | 95 |
| f | 150 | 12 | 6.98 | 10 | 5.81 | 0.128 | 2.42 | −1.3 | — | — | 25 | 7 | 92 | 95 |

Notes:
The current efficiency in run a is about 85%. For each of runs b-f, the current efficiency is about 80%.
[1]Theoretical minimum ratio for complete conversion of tet-acid to 3,6-D.

Example 8

A series of four runs (a–d) is made at different tet-acid to NaOH ratios, using a pre-cleaned and in-situ activated silver screen cathode which is periodically reactivated during the reduction.

To 300 ml of distilled water in a 600 ml glass beaker, a preselected weight of reagent grade NaOH is added with magnetic stirring, the temperature being controlled by a water bath at a preselected level. A planar, 20 mesh, silver screen cathode, 5 cm×7.5 cm, which has been immersed in a 1:1 mixture of water and c. aq. HCl for 10 minutes and rinsed with water, is completely immersed in the resulting base solution. A planar graphite anode of the same dimensions as the cathode is similarly immersed in the base solution and is spaced about 1 cm from the cathode. The cathode is subjected to a potential (relative to a saturated calomel reference electrode) which is initially just detectably positive and is then raised to about +0.6 volts over a period of several minutes. The polarity across the cell is then reversed and the cathode potential set at about −1.3 volts (cell voltage about 2 volts). 5 grams of tet-acid is then mascerated with a 20 ml portion of base solution (withdrawn from the cell) and the resulting slurry returned to the cell, the reducing being thereby initiated. The latter procedure is repeated until (2 hours) all of the tet-acid to be reduced (35 grams) has been introduced to the cell. The cathode is then reactivated, by a polarity reversal (to +0.6 volts) of about 3 minutes duration. The reduction is continued for a total time of 8 hours, the cathode being reactivated every 2 hours. The cell current increases from an initial level of about 3 amperes to about 5 amperes when the base solution becomes saturated with the tet-acid sodium salt, and then declines to a final level of about 0.3 amperes.

The cell contents are then worked up by acidification, extraction (3×) with CH$_2$Cl$_2$ and evaporation. (It is found that if the amount of CH$_2$Cl$_2$ used in the first extraction is not sufficient, an emulsion forms; however, this is readily broken by adding more CH$_2$Cl$_2$.)

Runs a–d are summarized in Table III below.

TABLE III
EFFECTS OF TET-ACID/NaOH RATIO AND TEMPERATURE

| Run | NaOH Wt. Grams | NaOH Wt. % | Tet-Acid[1] Wt. % | Initial Mole Ratio Tet-Acid NaOH | Final No. Ratio[2] OH$^-$/Cl$^-$ | Temp. °C. | Product % Theor. Yield | Product 3,6-D Content Wt. % |
|---|---|---|---|---|---|---|---|---|
| 8a | 33 | 8.9 | 9.5 | 0.163 | 1.58 | 38–40 | 94 | 97 |
| b | 22 | 6.2 | 9.8 | 0.244 | 0.55 | 38–40 | 91.5 | 94 |
| c | 17 | 4.8 | 9.9 | 0.316 | 0.085 | 38–40 | 88 | 87.5 |
| d | 33 | 8.9 | 9.5 | 0.163 | 1.58 | 27–30 | 93.5 | 97 |

Notes:
[1]Approx. 97% pure. Yields given are corrected accordingly.
[2]Theoretical minimum OH$^-$/Cl$^-$ ratio for 100% conversion of tet-acid to 3,6-D.

III. Operation of the Process of the Invention on a Pilot Plant Scale

"Standard" cell, conditions and procedure

A rectangular box having external dimensions of 5.125"×13"×48" (13 cm×33 cm×122 cm) was assembled from two 1"×13"×48" LUCITE ® backing plates, a pre-glued 3"×13"×48" frame formed from 1" thick LUCITE ®, two 1/16" thick×1" wide, rectangular Neoprene gaskets and forty 3/8"×1½" or 1¾" bolts. To the inner surface of one of the two backing plates a 1/16"×10⅞"×40" planar silver screen (20 mesh) was fastened by ten, uniformly spaced, silver-plated Monel, 9/16", individually-gasketed bolts passing through the backing plate. Similarly, a 2¾"×10⅞"×40" graphite anode was drilled and tapped (10 uniformly spaced holes) and fastened to the inner face of the other backing plate by rhodium-plated titanium bolts, leaving a ¼" gap between the anode and cathode. Through top and bottom openings in the cell (box), connections were made for circulation of liquid in a circuit comprising the cell (up-flow), a small heat exchanger, a sump (for addition of reactants) and a centrifugal pump. A saturated calomel reference electrode (in a Luggin capillary) was inserted through an additional opening in the cell top and positioned so it just touched the cathode. Electrical power for the cell was provided by a General Electric metallic rectifier (0–10 volts, 0–500 amperes) reversibly connected by leads to the protruding portions of the cathode and anode bolts.

The silver screen used (in most of the runs) had been pre-plated, in-situ, with silver, by filling the cell with a solution of 36 grams of AgNO₃ in about 5000 cc of 19% NH₄OH and cathodically polarizing the screen (potential vs. SCE, −0.05 to −0.13 volts; 16 amps) for 90 minutes, draining the cell and rinsing it out four times with distilled water.

The cell volume was about 4 liters and the system volume was about 23 liters, total.

Before each run, the entire system was rinsed with clean water and the cell was cleaned by filling it with (unless otherwise noted) 1:1 water/c. HCl—which was allowed to stand for ten minutes—then drained. The system was then re-rinsed and charged with NaOH and water, which was circulated briefly. With the pump turned on, the cathode voltage was gradually increased over a period of several minutes from 0 to about +0.6 volts (vs. the reference electrode) and the rectifier potential adjusted to hold this voltage for a few minutes. The polarity across the cell was then gradually reversed until the cathode potential was about −1.3 volts (total activation time about 10 minutes).

The NaOH used was either reagent grade pellets or was Mercury Cell 50% NaOH (Georgia Pacific Co.) and was dissolved in (or diluted with) purified water in such proportion that the initial NaOH content of the reaction mixture would be as desired (6–7 wt. %, typically).

A quantity of tet-acid (97% minimum assay) was ground with a portion of caustic solution withdrawn from the sump and the resulting mixture was processed with a Cowles disperser and returned to the sump. The pump was turned on, thereby circulating the tet-acid/caustic mixture through the cell (at a rate of about 38 to 95 liters/minute), and initiating the reduction.

The temperature of the reaction mixture was read at a point between the cell top and the heat exchanger and was maintained within a desired range by adjusting the flow of cooling water through the heat exchanger.

The weight of tet-acid charged to the reaction ranged from about 0.8 to about 1.6 times the weight of NaOH charged.

The average cell current ranged from about 98 to about 188 amperes, corresponding to nominal current densities of from about 0.036 to about 0.053 amps/cm² (taking the projected surface area of the cathode as 10⅞"×40"=435 in², or 2806.4 cm²). Since the cathode was a screen, the actual current densities probably ranged from about 0.05 to about 0.07 amps/cm². Initial cell currents were as high as about 315 amperes but the currents just prior to run termination were as low as about 16 amperes (depending on the temperature).

The course of each reaction was followed by sampling the cell (system) contents periodically and potentiometrically titrating for Cl⁻ content with 0.1 N AgNO₃ solution. When the rate of Cl⁻ content increase became very low and the current rate of Cl⁻ had dropped to a base-line value, the reaction was terminated and the system drained.

The composition of the reaction mixture was determined by gas phase chromatography (GPC). A 150 ml aliquot of the reaction mixture (usually an essentially homogeneous aqueous solution) was acidified to pH 1 and extracted three times with $CH_2Cl_2$. The combined extracts were dried over $Na_2SO_4$ and stripped in a rotary evaporator to a pot temperature of 45°–50° and the resulting solid (or semi-solid) residium dried in vacuo for 1 hour at 45° C., cooled and weighed. An approximately 0.1 gram sample was weighed out, combined with an equal weight of 1,2,3,4-tetrachlorobenzene (as an internal standard) and with 1 ml of BSA (N,O-bis(-trimethylsilyl)acetamide). The resulting mixture was heated in a REACTI-THERM ® reactor (Pierce Chemical Co.) for 10–15 minutes at 60° C., to convert the various picolinic acids to the corresponding trimethylsilyl esters. It was then injected in a GPC apparatus programmed for a pre-selected time/temperature profile-starting at 160° C. Detection was by means of thermal conductivity differences and the response factors for the several anticipated components of the sample had been pre-determined with pure standard samples.

Example 9 Preparation of 3,6-D

The essential data for nine runs (a–i) carried out in the preceding manner are given in Table IV, below. It should be noted that in calculating the % theoretical yields obtained in these runs, it was assumed that the overall weight loss experienced in the course of the reaction was entirely due to evolution of oxygen (which was generally not strictly correct). Also, the purity of the tet-acid starting material was taken as 97%, even though some of the tet-acid used assayed as high as 97.9%, because reliable assays were not available for all tet-acid supplied. Thus, apparent yields of 100% (or higher) obtained in some runs have been discounted (in Table IV) to a maximum value of 99%.

In addition to the amount of 3,6-D present in the final product, the contents of tet-acid, trichloropicolinic acids, monochloro-, 4,5-dichloro- and 4-hydroxy-3,5,6-trichloropicolinic acids present were also determined for some runs. However, only very minor amounts of the latter several impurities were found and columns are not provided for these minor components in the Table.

The theoretical minimum OH⁻/Cl⁻ number ratio calculated for each of the runs in the Table was about 0.6 and the actual final ratios, determined analytically, were in good agreement with this value.

TABLE IV

PILOT PLANT SCALE REDUCTIONS OF TETRACHLORO-2-PICOLINIC ACID

| Run | Total Grams H₂O, NaOH Tet-Acid | Wt. % Tet-Acid | Wt. % NaOH | Initial Mole Ratio Tet-Acid to NaOH | Reac. Temp. °C. | Cathode Potential Volts | Average Cell Current Amps | Current Efficiency % | Run Time Hrs. | % Theor. Yield Solids | Wt. % 3,6-D |
|---|---|---|---|---|---|---|---|---|---|---|---|
| 9a⁽¹⁾ | 22436 | 5.8 | 7.0 | 0.1270 | 28–30 | −1.28 | 98 | 79 | 6.5 | 98 | 95.1 |
| b⁽²⁾ | 22436 | 5.8 | 7.0 | 0.1270 | 23–30 | −1.25 | 105 | 71 | 6.5 | 92 | 98.0 |
| c | 23170 | 9.8 | 6.3 | 0.2385 | 8–37 | −1.28 | 112 | 75 | 11.0 | 99 | 97.9 |
| d | 23170 | 9.8 | 6.3 | 0.2385 | 20–35 | −1.28 | 111 | 69 | 11.5 | 97 | 97.0 |
| e⁽³⁾ | 23170 | 9.8 | 6.3 | 0.2385 | 19–35 | −1.28 | 119 | 77 | 10.0 | 99 | 96.6 |
| f⁽³⁾ | 23170 | 9.8 | 6.3 | 0.2385 | 16–35 | −1.30 | 84 | 73 | 14.5 | 99 | 96.0 |
| g⁽³⁾ | 23170 | 9.8 | 6.3 | 0.2385 | 15–35 | −1.29 | 104 | 80 | 11.0 | 99 | 98.0 |
| h⁽³⁾ | 23170 | 9.8 | 6.3 | 0.2385 | 11–35 | −1.29 | 135 | 76 | 9.0 | 99 | 94.5 |

TABLE IV-continued
PILOT PLANT SCALE REDUCTIONS OF TETRACHLORO-2-PICOLINIC ACID

| Run | Total Grams H₂O, NaOH Tet-Acid | Wt. % Tet-Acid | Wt. % NaOH | Initial Mole Ratio Tet-Acid to NaOH | Reac. Temp. °C. | Cathode Potential Volts | Average Cell Current Amps | Current Efficiency % | Run Time Hrs. | % Theor. Yield Solids | Wt. % 3,6-D |
|---|---|---|---|---|---|---|---|---|---|---|---|
| i[1],[3] | 23170 | 9.8 | 6.3 | 0.2385 | 16–36 | −1.29 | 151 | 72 | 8.3 | 99 | 95.1 |

Notes:
[1]Cathode not cleaned before run.
[2]Cathode (cell) cleaned with 1:9 c. HNO₃/H₂O.
[3]Cathode anodized in-situ at 4 hour intervals, during run.

Example 10 Effect of Metal Impurities in Aq. NaOH Used; Substantial Trichloro-acid Contents in Product Three runs (a–c) were carried out essentially as in Example 9, except that the cathode (cell) was not cleaned before any of these runs. The NaOH solution in each run was made up from 50% NaOH subsequently found to contain about 20 ppm of base-metals which are detrimental to the efficiency of silver cathodes for the production of 3,6-D. (An experimental silver screen cathode used 8 hours in a basic aqueous solution derived from the contaminated NaOH was found, by X-ray fluorescence, to have 16% of its surface occluded with iron, about 1% by nickel, 2.3% by copper and about 0.7% by lead and (perhaps) zinc.)

The conditions and results (including the content of trichloropicolinic acids in the product) for these runs are given in Table V, below. Again, the contents of by-products (other than the 4-hydroxy derivative of tet-acid) were negligible and are not given.

| Contact Time Hrs. | Cathode Potential Volts | Cell Current Amps |
|---|---|---|
| 6.3 | −1.00 | 0.1 |

The initial mole ratio of tet-acid to NaOH was 0.268 and the theoretical final OH⁻/Cl⁻ ratio was 0.364.

Work-up of the reaction mixture by acidification, CH₂Cl₂ extraction and evaporation gave 5.0 grams of solid product (vs. 5.2 grams theory for 3,6-D and 6.1 grams theory for 3,4,6-T and/or 3,5,6-T). GPC analysis showed the product to have the following composition: 3,6-D, 12.2 wt. %; monochloro-acid(s), 0.2%; trichloropicolinic acids, 81.5%; 4-hydroxy derivative of tet-acid, 0.5%; other materials 0.2%.

What is claimed is:

1. A process of electrolytic reduction in which a chlorine substituent in the 4- or 5-position of a polychloropicolinic acid which is tetrachloro-, 3,4,6-trichloro- or 3,5,6-trichloro-2-picolinic acid, is replaced with a hydrogen, said process comprising passing a direct, electrical current to a cathode from an anode through a stirred, basic aqueous solution of said picolinic acid, said cathode having a surface layer of silver microcrystals formed by the electrolytic reduction of colloidal, hydrous, silver oxide particles in the presence of an aqueous base.

2. The process of claim 1 in which said cathode has a potential, relative to a saturated calomel reference electrode, of from about −0.8 to about −1.8 volts.

3. The process of claim 1 in which said anode is a graphite anode.

4. The process of claim 1 in which an undivided body of said solution functions as both catholyte and anolyte.

5. The process of claim 1 in which said cathode is a silver screen.

6. The process of claim 2 in which said solution has a temperature within the range of from about 5° to about 60° C.

TABLE V
PRODUCTION OF MIXTURES OF 3,6-D AND TRICHLORO- PRECURSORS THEREOF, USING METALS-CONTAMINATED 50% NaOH

| Run | Total Grams H₂O, NaOH Tet-acid | Wt. % Tet-acid | Wt. % NaOH | Initial Mole Ratio Tet-acid to NaOH | Reac. Temp. °C. | Cathode Potential Volts | Average Current Amps | Current Efficiency % | Run Time Hrs. | % Theor. Yield Solids | Weight Percent of ||||
|---|---|---|---|---|---|---|---|---|---|---|---|---|---|---|
| | | | | | | | | | | | Tet-acid | Tri-acids[1] | 3,6-D | 4-Hydroxy[2] |
| 10a | 63880 | 3.4 | 4.1 | 0.1271 | 18–30 | −1.56 | 188 | <33 | 6.5 | — | 3.0 | 39.3 | 45.0 | 1.9 |
| b | 24850 | 1.0 | 7.2 | 0.0213 | 25–31 | −1.26 | 22 | <38 | 7.0 | — | 8.6 | 23.8 | 57.8 | 2.7 |
| c | 5160 | 5.8 | 7.0 | 0.1271 | 22–26 | −1.27 | 12 | 16 | 24.0 | 78 | 6.2 | 34.6 | 49.4 | ND[3] |

Notes:
[1]About 99% 3,5,6-T and 1% 3,4,6-T.
[2]3,5,6-Trichloro-4-hydroxy-2-picolinic acid.
[3]None detecatable.

IV. Laboratory Scale Preparation of Trichloro Acids

Example 11 Effect of Lower Cathode Potential and Higher Temperature on Product Composition A mixture of 8 grams of 50% NaOH (contaminated with base-metals, as in Example 10), 100 cc water and 7 grams of tet-acid was electrolyzed for about 6 hours at a temperature of 40° C., using a freshly anodized, new silver screen cathode and a graphite anode. The cathode potential and cell current after successively longer contact times were as follows:

| Contact Time Hrs. | Cathode Potential Volts | Cell Current Amps |
|---|---|---|
| 0 | −1.00 | 0.8 |
| 1.5 | −1.00 | 0.8 |
| 3.5 | −1.00 | 0.6 |
| 5.5 | −1.00 | 0.1 |

7. The process of claim 6 in which said solution has a pH of at least 13 and contains at least 0.08 hydroxyl ions per chloride ion present therein.

8. The process of claim 2 in which the anode has a positive potential, relative to said cathode, such that the density of said current is from about 0.005 to about 0.085 amperes per cm² of projected cathode surface.

9. The process of claim 4 in which:
   a. said solution is saturated with the base salt of said picolinic acid, and, together with undissolved particles of the acid, constitutes a slurry,
   b. initially, all of said acid, as said salt and as said particles, to be charged, and all of the base to be charged, are present in the slurry,
   c. initially, the number of moles of said acid and salt per equivalent of hydroxyl is within the range of from about 0.1 to about 0.2, and
   d. the electrolysis is continued until at least 90% of the acid charged to the reaction has been converted to the corresponding base salt of 3,6-dichloro-2-picolinic acid.

10. The process of claim 1 in which a portion of the active silver layer on the cathode is occluded by base metals, said picolinic acid is tetrachloro-2-picolinic acid, and the reduction is continued until the ratio of trichloro-picolinic acids to 3,6-dichloropicolinic acid in the reaction mixture has attained a maximum.

11. The process of claim 10, carried out at a cathode potential of from about −0.8 to about −1.2 volts.

12. The process of claim 1 in which more of the polychloropicolinic acid to be reduced, and/or more of the base employed, is added to said solution after at least a portion of said acid(s) originally charged to the reaction has been reduced.

13. The process of claim 1 in which said solution is formed by dissolving said polychloropicolinic acid in aqueous NaOH.

14. The process of claim 1 in which said polychloropicolinic acid is tetrachloro-2-picolinic acid and the reduction is continued until 3,6-dichloro-2-picolinate anions constitute at least 90 mole percent of the chlorinated picolinate anions present in the reaction mixture.

15. The process of claim 1, operated for the coproduction of oxygen and polychloropicolinate anions of the structure

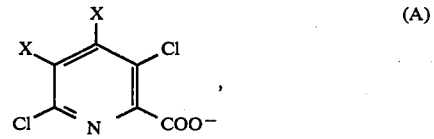

wherein one X is H and the other is H or Cl,
said process comprising,
providing a solution in water of a hydroxyl ion source-material and a polychloropicolinic acid of the structure

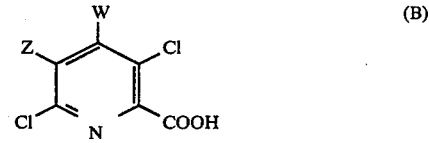

wherein both Z and W are Cl, or one is Cl and the other is H,
immersing a cathode in a body of said solution and, while agitating said body, passing an electric current therethrough from an anode to the cathode,
said body of solution having a temperature within the range of from about 5° to about 60° C., a pH of at least 13, and containing at least 0.08 hydroxyl ions per chloride ion present therein,
said cathode comprising a shaped, electrical conductor in intimate contact with a water and hydroxyl ion-containing, immobilized, metastable layer of aggregated silver microcrystals formed by electrolytic reduction of colloidal, hydrous, silver oxide particles in the presence of water and hydroxyl ions, the cathode having a potential, relative to a saturated calomel reference electrode, of from about −0.8 to about −1.8 volts, and
said anode having a positive potential, relative to the cathode, such that the density of said current is from about 0.005 to about 0.085 amperes per cm² of projected cathode surface,
thereby forming anions of said polychloropicolinic acid (A) at said cathode and oxygen at said anode.

* * * * *

UNITED STATES PATENT AND TRADEMARK OFFICE
CERTIFICATE OF CORRECTION

PATENT NO. : 4,217,185
DATED : August 12, 1980
INVENTOR(S) : D. Kyriacou, F. Y. Edamura and J. Love It is certified that error appears in the above-identified patent and that said Letters Patent are hereby corrected as shown below:

Column 3, compound (IV) at line 30 is wrongly identified as "(3,4,6-T) anion"; should be --(3,5,6-T) anion--;

Column 8, line 47, "electrolyte" should be --electrolytic--;

Columns 19 and 20, Table II, the sub-heading "Final$^{(1)}$" should be over the sub-heading "No. Ratio $OH^-/Cl^-$" rather than over "Current Amps";

Signed and Sealed this

Twentieth Day of January 1981

[SEAL]

Attest:

Attesting Officer

RENE D. TEGTMEYER

Acting Commissioner of Patents and Trademarks